(12) United States Patent
Heintz et al.

(10) Patent No.: US 7,030,091 B2
(45) Date of Patent: Apr. 18, 2006

(54) NON-AQUEOUS INJECTABLE FORMULATION PREPARATION WITH PH ADJUSTED FOR EXTENDED RELEASE OF SOMATOTROPIN

(75) Inventors: Daniel N. Heintz, St. Louis, MO (US); Yunhua N. Jeng, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 326 days.

(21) Appl. No.: 10/691,425

(22) Filed: Oct. 22, 2003

(65) Prior Publication Data

US 2004/0087495 A1  May 6, 2004

Related U.S. Application Data

(62) Division of application No. 09/894,058, filed on Jun. 28, 2001, now Pat. No. 6,664,234.

(60) Provisional application No. 60/215,599, filed on Jun. 30, 2000.

(51) Int. Cl.
*A61K 38/00* (2006.01)
(52) U.S. Cl. ..................................................... 514/21
(58) Field of Classification Search ...................... None
See application file for complete search history.

(56) References Cited

U.S. PATENT DOCUMENTS

| | | | |
|---|---|---|---|
| 4,816,568 A | 3/1989 | Hamilton et al. | 530/399 |
| 4,857,506 A | 8/1989 | Tyle | 514/12 |
| 4,917,685 A | 4/1990 | Viswanathan et al. | 604/891.1 |
| 4,977,140 A | 12/1990 | Ferguson et al. | 514/12 |
| 5,034,229 A | 7/1991 | Magruder et al. | 424/422 |
| 5,037,420 A | 8/1991 | Magruder et al. | |
| 5,096,885 A | 3/1992 | Pearlman et al. | |
| 5,219,572 A | 6/1993 | Sivaramakrishnan et al. | 424/438 |
| 5,356,635 A | 10/1994 | Raman et al. | 424/484 |
| 5,359,030 A | 10/1994 | Ekwuribe | 530/303 |
| 5,399,489 A | 3/1995 | Krivi | 435/69.4 |
| 5,438,040 A | 8/1995 | Ekwuribe | 514/3 |
| 5,474,980 A | 12/1995 | Mitchell | |
| 5,520,927 A | 5/1996 | Kim et al. | 424/450 |
| 5,607,691 A | 3/1997 | Hale | |
| 5,612,315 A | 3/1997 | Pikal et al. | 514/21 |
| 5,631,227 A | 5/1997 | Harbour | 514/12 |
| 5,681,811 A | 10/1997 | Ekwuribe | 514/8 |
| 5,739,108 A | 4/1998 | Mitchell | 514/12 |
| 5,744,163 A | 4/1998 | Kim et al. | 424/489 |
| 5,773,588 A | 6/1998 | Owsley et al. | |
| 5,801,141 A | 9/1998 | Steber et al. | |
| 5,849,704 A | 12/1998 | Sørensen et al | 514/12 |
| 5,972,370 A | 10/1999 | Echenhoff | 424/424 |
| 5,986,073 A | 11/1999 | Storrs et al. | 530/419 |
| 6,086,918 A | 7/2000 | Stern | 424/474 |
| 6,162,258 A | 12/2000 | Scarborough | |

FOREIGN PATENT DOCUMENTS

| | | |
|---|---|---|
| EP | 0 216 485 | 4/1987 |
| EP | 0 278 103 A | 8/1988 |
| EP | 0 303 746 A1 | 2/1989 |
| EP | 0 374 120 A | 6/1990 |
| EP | 0 523 330 A1 | 1/1993 |
| EP | 0 913 177 | 5/1999 |
| JP | 3086834 | 4/1991 |
| WO | WO 89 09614 A | 10/1989 |
| WO | WO 93/12812 | 7/1993 |
| WO | WO 93/13792 | 7/1993 |
| WO | WO 93/19773 | 10/1993 |
| WO | WO 97/03692 | 2/1997 |
| WO | WO 97/29767 | 8/1997 |
| WO | WO 98/29131 | 7/1998 |
| WO | WO 00/13674 | 3/2000 |

OTHER PUBLICATIONS

Katakam, Manohar: *Use of non-ionic surfactants to stabilize recombinant human growth hormone and to develop its sustained release formulation*, Diss. Abstr. Int., vol. 57, No. 5, 1996, p. 3149.

*Primary Examiner*—Bruce R. Campell
*Assistant Examiner*—Roy Teller
(74) *Attorney, Agent, or Firm*—Grace L. Bonner; Howrey LLP

(57) ABSTRACT

The present invention provides compositions of matter which allow for the extended release and enhanced bioavailability of biologically-active polypeptides following parenteral delivery to an animal. More particularly, it concerns compositions comprising biologically-active somatotropin formulated for extended release, methods of preparing these compositions, and methods of using the same. These compositions comprise somatotropin, a pH-adjusting constituent (PAC), and a substantially non-aqueous, hydrophobic excipient. The PAC may comprise any suitable, biocompatible compound including, but not limited to one or mixtures of two or more of the following: acetic acid, phosphoric acid, monobasic phosphate. The PAC is added to the compositions of matter in an amount effective to adjust the pH to or near to the isoelectric point (pI) of the somatotropin component.

22 Claims, 5 Drawing Sheets

Figure 1: Comparison of bST Release Profiles in Rodents
Formulation Lot NBP6207845-E vs POSILAC
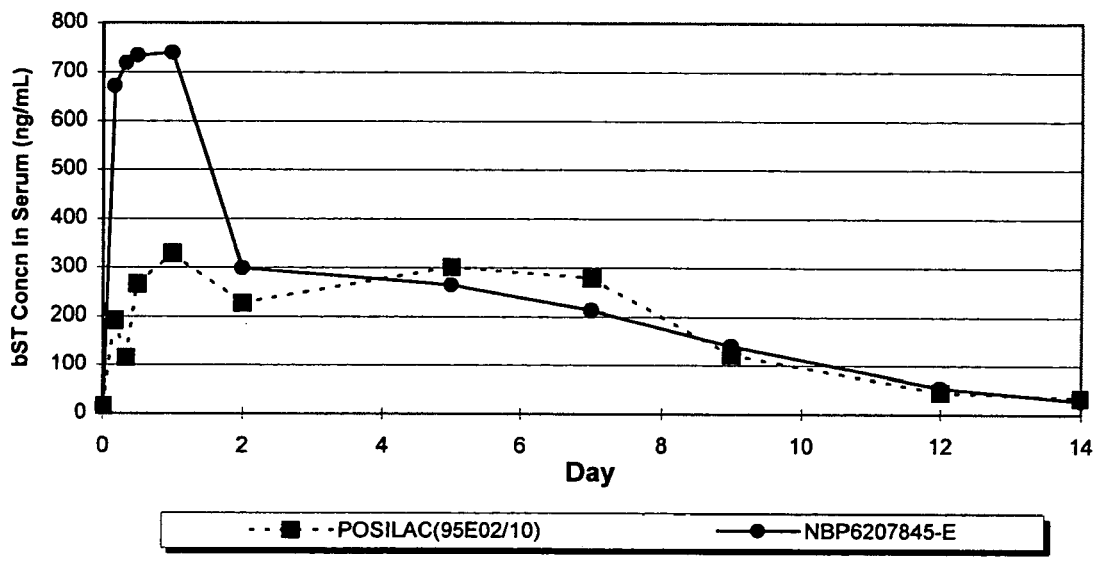
Figure 2 : Comparison of bST Release Profiles in Calves
Formulation Lot 6207845-E vs POSILAC
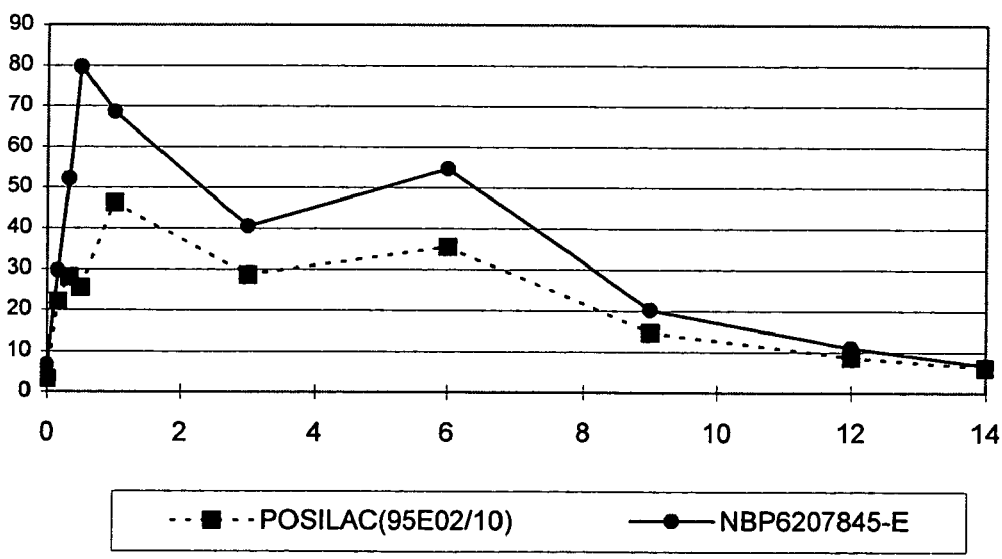

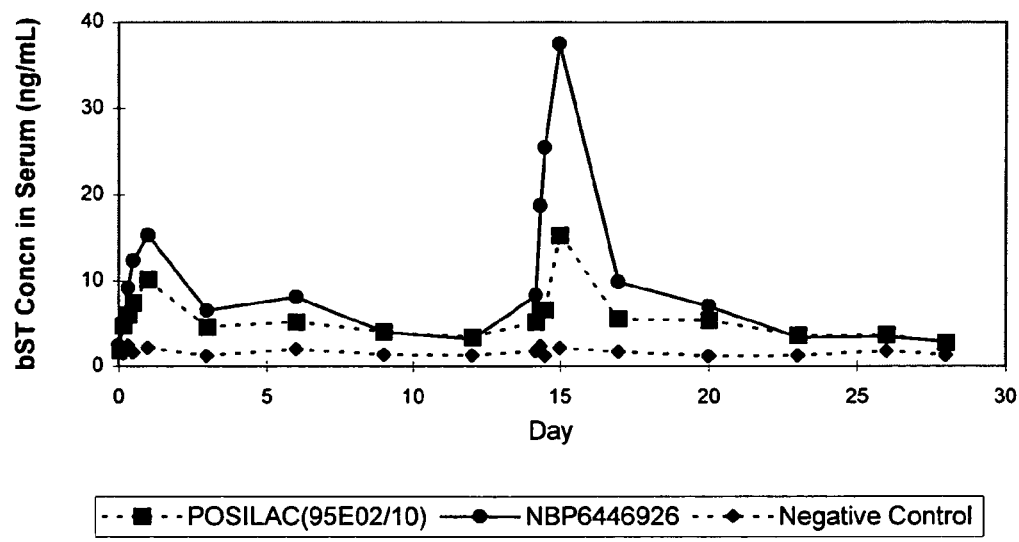
Figur 3 : Comparison of bST Rel as Profiles in Cows
Formulation Lot NBP6446926 vs POSILAC
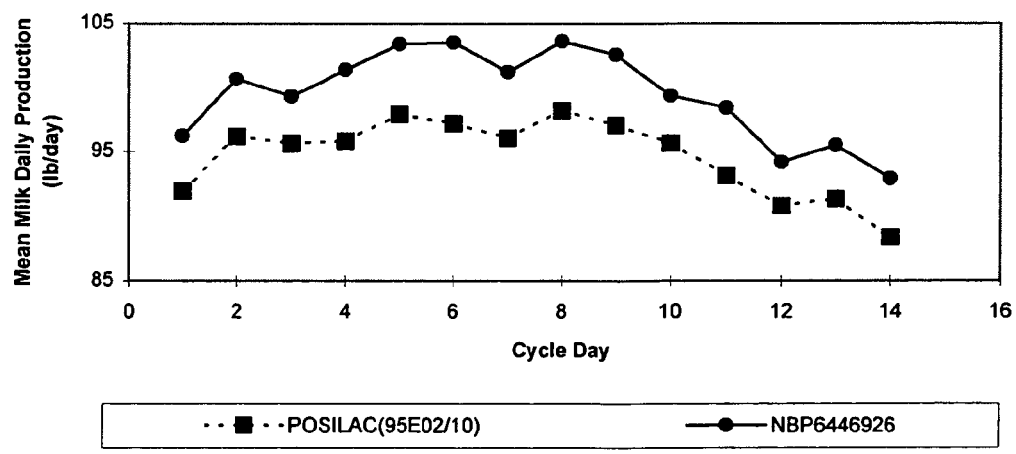
Fig 4 : Comparison of Milk Profiles in Cows
Formulation Lot NBP6446926 vs POSILAC Figure 5 :   Flow diagram showing adjustment of ST solution pH using an Acid.
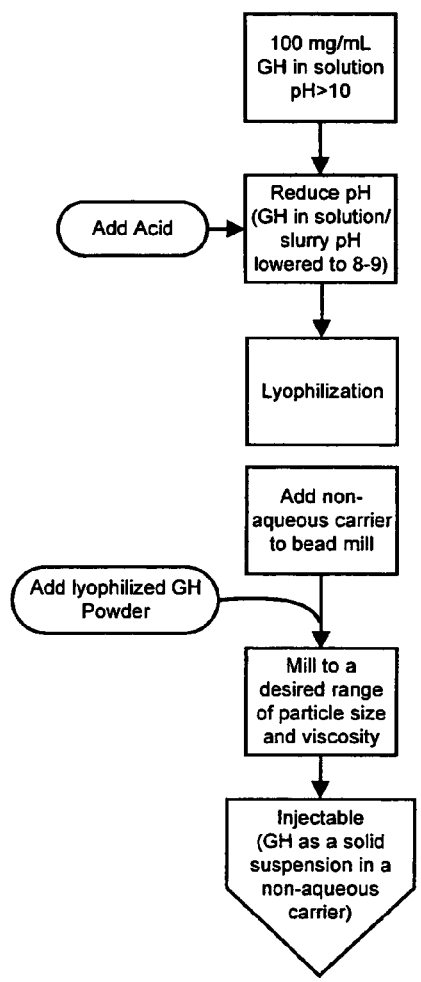

Figure 6 :   Flow diagram showing the adjustment of ST solution pH using a salt.
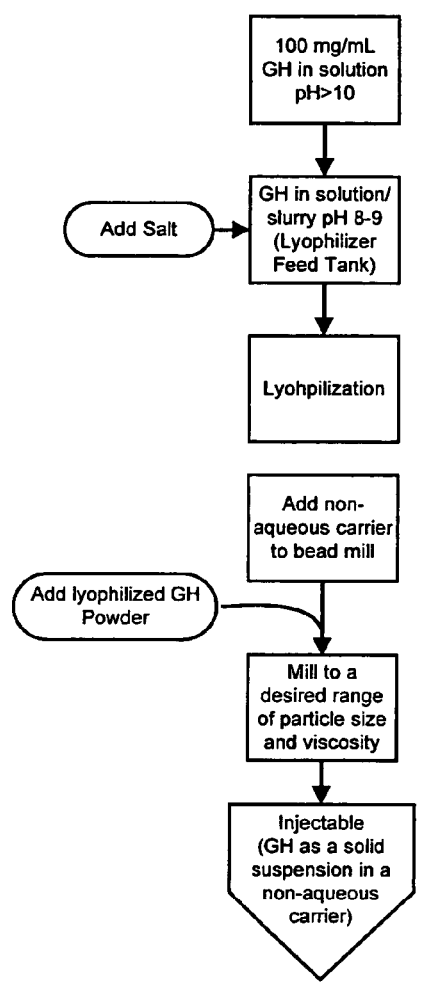

Figure 7: Flow diagram showing adjustment of ST solution pH by the addition of an acidic salt.
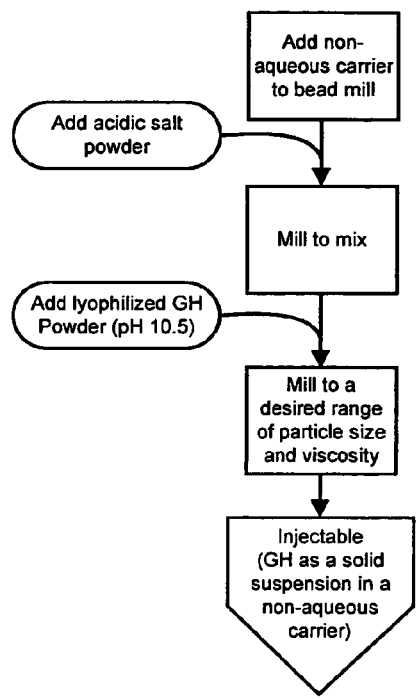

NON-AQUEOUS INJECTABLE FORMULATION PREPARATION WITH PH ADJUSTED FOR EXTENDED RELEASE OF SOMATOTROPIN

This is a divisional application of application Ser. No. 09/894,058, filed Jun. 28, 2001, now S. Pat. No. 6,664,234 that claims the benefit of Provisional Application Ser. No. 60/215,599 filed Jun. 30, 2000.

BACKGROUND OF THE INVENTION

1. Field of the Invention

The present invention relates to the field of biologically-active somatotropin compositions. More particularly, it concerns biologically-active compositions of somatotropin formulated for extended release into the bloodstream of an animal following parenteral administration, methods of preparing these compositions, and methods of using the same.

2. Technical Problem Addressed by the Invention

Although prolonged activity of some biologically active (bioactive) polypeptides can be achieved by parenterally administering only very small doses, others are required in sufficient serum concentrations and/or have such a short half-life in serum that a substantial dose must be administered to provide the desired biological effect over an extended time such as a week or longer. Somatotropins (growth hormones) are an example of such polypeptides.

To prevent undesirably rapid release into an animal's bloodstream, certain polypeptides have been parenterally administered in liquid vehicles which may optionally contain hydration retardants (antihydration agents) or in association with metals or metal compounds that further lower their solubility in body fluids. To avoid the need for unacceptably large quantities of such a vehicle, and for other reasons including superior prolonged release performance, it is advantageous to employ substantial concentrations of the polypeptide in the vehicle, e.g., as shown in U.S. Pat. No. 5,739,108 to James C. Mitchell, U.S. Pat. No. 4,977,140, assigned to Eli Lilly, U.S. Pat. No. 5,520,927, assigned to Lucky, Ltd., and U.S. Pat. No. 5,744,163, assigned to LG Chemicals Ltd. However, there has been a need to improve the efficiency with which such polypeptides are released into the animal's bloodstream in a biologically active form ("bioavailability") and/or, in some utilities, their effectiveness in providing the desired physiological response in the animal ("efficacy"). Each of these factors can substantially affect the amount of the polypeptide that must be administered to achieve the desired biological effect, and consequently, the cost of each administration. Typically, polypeptides such as somatotropins are made in prokaryotic organisms that have been transformed using recombinant DNA, such that even small quantities are very expensive to produce in the pure forms required for product safety and regulatory approval.

3. Description of Related Art

There is currently a substantial body of work which addresses the need for protein formulations which provide for extended release of biologically active polypeptides, including somatotropins. This body of work includes a number of publications describing the use of various stabilizing compounds and excipients. Furthermore, various methods of and devices for administering the bioactive compositions have also been reported in the existing art. Exemplary publications which address this technological problem include the following:

Christensen et al., WO 97/03692, discloses a formulation of growth hormone with zinc, and optionally lysine or calcium, ions. The formulation can contain an excipient such as a disaccharide, a polysaccharide, or a sugar alcohol. Growth hormone so formulated showed resistance to deamidation.

Dong et al., WO 00/13674, discloses a mechanism for timed-release of a drug. The mechanism comprises a semi-permeable walled container that houses a capsule, which capsule comprises a drug formulation, a piston, and an osmotic composition. The dosage mechanism releases the drug formulation through a passageway at a controlled rate over a period of up to 24 hours.

Ekwuribe, U.S. Pat. Nos. 5,359,030, 5,438,040, and 5,681,811 disclose a stabilized conjugated peptide complex comprising a peptide conjugatively coupled to a polymer including lipophilic and hydrophilic moieties which is suitable for both parenteral and non-parenteral administration.

Ferguson et al., U.S. Pat. No. 4,977,140, discloses a sustained release formulation comprising bovine somatotropin in a carrier comprising a wax (about 1%–20% by weight) and an oil (about 80%–99% by weight). On injecting into a dairy cow, the formulation led to greater milk production for 28 days.

Hamilton et al., U.S. Pat. No. 4,816,568, discloses compositions of animal growth hormones and stabilizers. The stabilizers are soluble in aqueous solutions, and generally are very polar. The stabilizers taught include polyols, amino acids, amino acid polymers with charged side groups at physiological pH, and choline derivatives. An aqueous formulation of the composition can be formed by (i) dispersing the stabilizer in an aqueous solution and (ii) subsequently adding the growth hormone. A solid formulation can be formed by (i) mixing the stabilizer and the growth hormone, (ii) optionally adding adjuvants, binders, etc. to the composition, and (iii) compressing the composition to form a tablet or pellet.

Kim et al., U.S. Pat. No. 5,520,927, discloses a parenterally administered, slow releasing bioactive pharmaceutical composition comprising somatotropin, at least one tocopherol compound, and a release delaying agent.

Kim et al., U.S. Pat. No. 5,744,163, discloses a formulation for the sustained release of animal growth hormone. The formulation comprises coating somatotropin containing pellets with a film of biodegradable polymer and a polyoxamer.

Magruder et al., U.S. Pat. No. 5,034,229, discloses a device for delivering a beneficial agent, e.g. a growth hormone, to an animal. The device can also deliver a polyol as a viscosity modulating means.

Martin, EP 0 216 485, discloses a method of preparing growth hormones complexed with transition metals. Methods for promoting growth in animals by treating them with transition metal complexed growth hormones are also described.

Mitchell, U.S. Pat. No. 5,739,108, discloses extended-release formulations of bioactive polypeptides comprising the polypeptide at from about 10% by weight to about 50% by weight in a dispersion in a biocompatible oil. The polypeptide can be associated with a non-toxic metal or metal salt. The formulation can also comprise an antihydration agent, such as aluminum monostearate.

Pikal, et al., U.S. Pat. No. 5,612,315, discloses formulations for the parenteral administration of human growth hormone comprising human growth hormone, glycine, and mannitol. The disclosed formulations are described as providing stabilization against protein aggregation.

Raman et al., U.S. Pat. No. 5,356,635, discloses a sustained release composition comprising a biologically active agent, e.g. somatotropin; a biodegradable, amorphous carbohydrate glass matrix, throughout which the e.g. somatotropin is dispersed; and a hydrophobic substance. The amorphous carbohydrate glass matrix comprises an amorphous carbohydrate and a recrystallization retarding agent, and makes up from about 60% by weight to 90% by weight of the composition. The composition is solid down to at least about 18° C.

Raman et al., WO 93/13792, discloses an implantable device comprising a transition metal-somatotropin complex in combination with a transition metal-solubilizing substance. The transition metal can be zinc, manganese, or copper. The metal-solubilizing substance can be an amino acid. Sucrose can be used to stabilize the somatotropin. The device can comprise silicone tubing or wax.

Seely et al., WO 93/19773, discloses aqueous solutions comprising (i) a lyophilized somatotropin composition comprising somatotropin and arginine HCl and (ii) a diluent comprising EDTA, nonionic surfactant, and optionally buffer or a non-buffering agent such as sucrose or trehalose.

Sivaramakrishnan et al., U.S. Pat. No. 5,219,572, discloses a device for controlled release of macromolecular proteins, e.g. somatotropin. The device comprises a water-soluble outer capsule completely surrounding an inner compartment containing non-uniform beadlets. The beadlets comprise a wax shell which surrounds a core matrix. The core matrix comprises e.g. somatotropin and optionally excipients, stabilizers, binders, and the like, e.g. magnesium stearate or sucrose. Upon dissolution of the outer capsule in the fluid environment in an animal, the beadlets are exposed to the fluid environment, and rupture at various times after exposure.

Sørensen et al., WO 93/12812, teaches that growth hormone can be stabilized by the presence of histidine or a histidine derivative. If the growth hormone is lyophilized, the composition can also comprise a bulking agent, i.e. sugar alcohols, disaccharides, and mixtures thereof.

Sørensen et al., U.S. Pat. No. 5,849,704, discloses a pharmaceutical formulation comprising a growth hormone and histidine or a derivative of histidine as an additive or buffering substance added to provide stability against deamidation, oxidation or cleavage of the peptide bonds in the growth hormone. Also disclosed is that crystallization of growth hormone in the presence of histidine or a derivative thereof gives rise to a higher yield of crystals having higher purity than known methods.

Steber et al., EP 0 523 330 A1, discloses a compacted, indented, partially-coated, implantable composition comprising a biologically active polypeptide (e.g. somatotropin); a fat, wax, or mixture thereof; and a sugar (e.g. mono-, di-, or trisaccharides).

Storrs, et al. U.S. Pat. No. 5,986,073, discloses a method for purifying and recovering biologically active somatotropin monomers. This work is based on the discovery that somatotropin monomers and somatotropin oligomers having overlapping isolelectric points may nevertheless be separated by selective precipitation over a very narrow pH range. Undesirable impurities are removed by this process and the purified somatotropin monomers recovered are suitable for parenteral application to target animals without further purification.

Tyle, U.S. Pat. No. 4,857,506, discloses a multiple water-in-oil-in-water emulsion for the sustained release of a growth hormone. The growth hormone is dispersed in an internal aqueous phase; the internal aqueous phase is dispersed in a water-immiscible liquid or oil phase; and the water-immiscible phase is dispersed in an external aqueous phase. The internal aqueous phase can include up to 40% by weight polyol, glycol, or sugar.

Viswanathan et al., U.S. Pat. No. 4,917,685, discloses a delivery device for a stabilized animal growth hormone. The device comprises a wall which surrounds and defines a reservoir. At least a portion of the wall is porous, to allow passage of growth hormone and stabilizer. The growth hormone and stabilizer formulation is substantially that disclosed by Hamilton et al., described above.

Despite the efforts described in the publications summarized above, there is still room for significant improvement of the technology. The present invention satisfies this need by providing improved, sustained release formulation of a somatotropin which has the advantages of providing both higher and more sustained levels of somatotropin in the serum of animals treated with these formulations.

The art summarized above discloses formulations in which the ingredients are present as solutes in aqueous solutions or as solids in tablets or pellets. The present invention describes non-aqueous injectable formulations in which solid, dry solids are suspended in a substantially non-aqueous carrier. Treatment of cattle, with the formulations described herein, leads to an extended response to the new formulations in treated animals thereby producing, inter alia, surprisingly increased milk production or increased weight gain.

SUMMARY OF THE INVENTION

The present invention provides for a composition of matter, which provides both for higher serum levels of somatotropin ("ST") and for a prolonged maintenance of those higher serum ST levels, compared to known formulations containing the same dose of somatotropin. Furthermore, these formulations have been demonstrated to also have superior efficacy for inducing weight gain or milk production when compared with currently available formulations containing the same amount of somatotropin but lacking a "PAC" as described herein. The ST formulations of the present invention have been demonstrated to be particularly effective for sustaining elevated milk production, compared to previously available formulations.

The formulations of the present invention provide for compositions of matter which comprise somatotropin and a pH-adjusting constituent (PAC), wherein the somatotropin's pH has been adjusted to a pH at or near its isoelectric point, at such time as the composition becomes aqueous. These pH-adjusted ST compositions provide for enhanced bioavailability of the ST following parenteral administration of the compositions (where "bioavailability" is the net result of the release, absorption, elimination, degradation and other physiological processes for a substance).

In various embodiments of the invention the pH-adjusted ST is suspended in a substantially non-aqueous hydrophobic carrier which yields a formulation which is fluidly injectable at the body temperature of the animal to be injected (typically 37–39° C.), and preferably injectable at temperatures no higher than 25° C. The compositions of the instant invention may be of any viscosity which is compatible with the present invention. In a preferred embodiment the viscosity of the composition is between about 500 and about 10,000 centipoise at 141 $s^{-1}$. An exemplary carrier considered for use in the present invention is a mixture of 95% sesame oil and 5% aluminum monostearate According to the present invention the ST used in the formulations may be from any origin which is suitable for use with the invention, including, but not limited to, native and/or recombinant bovine, porcine, equine, or human somatotropin.

In an alternative embodiment, pH adjustment can be achieved by adding either solid acids or salts, solutions of said acids or salts or any combination thereof. All biocompatible (non-toxic) acids and salts which are capable of effectively adjusting the pH to the desired range are considered useful in the present invention. Examples of pH-adjusting compounds considered useful for the present invention include, but are not limited to, acetic acid, phosphoric acid, monobasic phosphate, histidine-HCl, and mixtures thereof.

The present invention also provides a method of preparing the described compositions of matter. According to such an embodiment of the present invention the ST is provided as a lyophilized dry solid (for an example of preparing the lyophilized ST see U.S. Pat. No. 5,013,713, which is incorporated herein by reference). As used herein, the term "lyophilization" includes spray-drying and similar techniques for producing an essentially dry, finely particulate solid form of the ST.

The pH adjustment of the composition can be achieved by adding the PAC in any form compatible with the present invention, including as a dry solid, a solution, or a slurry added to a ST solution or slurry prior to lyophilization of the ST. Alternatively, the solid, dry salts or acids, such as monobasic phosphate or histidine-HCl may be added directly to the dry solid, lyophilized ST before or during its suspension in a hydrophobic carrier.

Another embodiment of the present invention provides a method for inducing improved weight gain or elevated milk production in a mammal. This method comprises parenterally administering an ST formulation of the present invention into the target mammal.

Yet another embodiment of the present invention provides a method for sustaining the elevated milk production response in a lactating mammal. Specifically, this comprises sustaining the elevated milk production (induced by the exogenous ST) for a longer time period and/or at a higher level (given the same serum ST concentration) than is possible with ST formulations which are currently available. This method comprises parenterally administering to the target mammal with a biocompatible ST formulation according to the present invention, wherein the ST present in the formulation is active in the target mammal.

According to the present invention these compositions and methods may be better understood by a review of the detailed description in conjunction with the drawings, which serve to facilitate the further illustration of certain aspects and/or certain embodiments of the invention.

DEFINITIONS

The following definitions are provided in order to aid those skilled in the art to understand the detailed description of the present invention.

Throughout the specification, unless otherwise indicated, percentages of compositions are by weight and temperatures are in degrees Celsius (° C.).

As used in the specification and claims, the term "substantially non-aqueous" means essentially anhydrous or containing water in such low proportion that it does not intolerably accelerate release of the polypeptide in the animal. Although this proportion of water may vary with each composition of the invention it is most commonly less than about 2% and most typically less than about 1%.

The term "non-toxic" as used herein refers to components of compositions that are reasonably safe and/or innocuous when used in appropriate amounts and under appropriate conditions in parenteral administration of such compositions as are described herein.

The term "biologically-active" or "bioactive" polypeptide or protein (e.g. somatotropin) is used herein to describe a polypeptide or protein, which following appropriate parenteral administration to an animal, has a demonstrable effect on a biological process of that animal. The effect may be hormonal, nutritive, therapeutic, prophylactic, or otherwise, and may mimic, complement, or inhibit a naturally occurring biological process. Although there is a vast array of potentially regulatable biological activities or processes, the following are mentioned as exemplary: stimulation of growth or lactation, and enhancement of the efficiency of feed usage.

The term "biocompatible", as used herein, refers to substances which have no intolerable adverse effect on the somatotropin, the animal, or, in the case of animals whose products enter the food chain, the consumers of such products.

"At such time as the composition becomes aqueous" as used herein with regards the disclosed compositions of matter, refers to the parameters which would be extant if the compositions were dissolved in water or an aqueous (non-buffered) solution, either in the formulating of the compositions or when the composition is resident in vivo after being parenterally administered to an animal.

"Sustaining elevated milk production response" or "sustained elevated milk production response", as used herein, refers to the ability of lactating animals to maintain an elevated level of milk production, over a period of time, despite decreasing serum levels of somatotropin.

BRIEF DESCRIPTION OF THE DRAWINGS

FIG. 1 is a graph showing the serum bovine somatotropin ("bST") levels over time in rodents treated with a bST composition which contained phosphoric acid as the PAC.

FIG. 2 is a graph showing the serum bST levels over time in calves treated with a bST composition containing phosphoric acid as the PAC.

FIG. 3 is a graph showing the serum bST levels over time in cows treated with a bST composition containing phosphoric acid as the PAC.

FIG. 4 is a graph showing the mean daily milk production, as averages over six consecutive 14-day administration cycles, in lactating cows treated with either POSILAC® or with a bST composition comprising phosphoric acid as the PAC.

FIG. 5 is a flow diagram showing one embodiment of the method of the present invention, wherein the pH adjusting constituent is an acid.

FIG. 6 is a flow diagram showing an alternative embodiment of the method of the present invention, wherein the pH adjusting constituent is salt.

FIG. 7 is a flow diagram showing an alternative embodiment of the method of the present invention, wherein the pH adjusting constituent is an acidic salt.

DESCRIPTION OF PREFERRED EMBODIMENTS

The present invention provides an injectable (or otherwise parenterally administerable) enhanced bioavailability formulation comprising: (i) a dry solid native or recombinant protein growth hormone (GH, synonymous with somatotropin, herein sometimes abbreviated as ST), and (ii) a dry, solid pH-adjusting constituent (PAC). Both the ST and PAC are suspended in an excipient comprised of a substantially non-aqueous oil, fat, or other hydrophobic substance that is at least partially liquid to creamy and/or biodegradable in an animal at the animal's body temperature and which is biocompatible with the animal. The suspension may be made in any order compatible with the invention.

Somatotropins from man and from the common domestic animals are proteins of approximately 191 amino acids, which are synthesized and secreted by the anterior lobe of the pituitary gland. Mature full-length human ST (hST) consists of 191 amino acids. ST is a key hormone involved in the coordination of somatic growth through the regulation of the metabolic processing of proteins, carbohydrates, and lipids. A major known effect of ST is the promotion of growth in organ systems which include, but are not limited to, the skeleton, connective tissue, muscles, and viscera such as the liver, intestine, and kidneys.

Growth hormones suitable for use in the present invention include, but are not limited to, somatotropins from human, bovine, equine, ovine, porcine, caprine, and avian sources. Preferably the ST is human, equine, bovine, or porcine ST. Even more preferably the ST is bovine ST (bST) or human ST (hST).

Somatotropin for use in the present invention can be obtained by extraction and subsequent concentration from the pituitary glands of various animals. Alternatively, ST may be produced using recombinant DNA techniques which are well understood and commonly used by those skilled in the art.

Somatotropins prepared using recombinant DNA techniques suitable for use according to the present invention may be produced by genetically transformed microorganism such as *E. coli*, or other bacteria, or by yeasts. Recombinant ST may also be produced by tissue culture or by a transgenic multicellular organism.

Somatotropins produced using molecular biological techniques may have an amino acid sequence identical to naturally occurring somatotropin. Alternatively, the somatotropin used may be an ST analog comprising one or more variations in amino acid sequence with respect to the native hormone. These amino acid variations may provide enhanced biological activity or some other biological or logistical advantages.

ST is usually synthesized in its native organism as an inactive precursor molecule which is processed to the mature, active form of the hormone via cleavage of an N-terminal signal peptide (26 amino acids in humans, 26–27 amino acids in cows). In order to express bioactive ST protein using recombinant DNA technology it may be advantageous to add, change, or delete one or more amino acids from the polypeptide. Such modifications, which do not overly diminish the activity of the ST, or make it biologically incompatible with the animal to be treated, are useful in the present invention. For example it may be useful to produce an ST polypeptide which contains a methionine residue at its N-terminus (N-terminal to the phenylalanine residue which is typically the first amino acid in the mature, active form the native hormone), resulting from microbial translation of the AUG start codon in a recombinant gene for the polypeptide (this form of ST is known as N-methionyl-ST). Another derivative envisioned for use in the present invention is N-alanyl-ST, which is similar to N-methionyl-ST except it begins with an N-terminal alanine residue (See Krivi U.S. Pat. No. 5,399,489, which is incorporated herein by reference) rather than an N-terminal methionine. Yet another derivative envisioned for use in the formulations described herein is N-phenylalanyl-ST which is analogous with the above polypeptides in that it begins with an N-terminal phenylalanine. N-phenylalanyl-ST results from the enzymatic removal of the N-terminal alanine from the N-alanyl-ST described above (see U.S. application Ser. No. 09/541844, which are herein incorporated by reference insofar as necessary to support enablement of N-phenylalanyl-ST). In one preferred embodiment of the current invention, the ST used, in the pH-adjusted ST formulation, is N-methionyl-bST.

In various embodiments of the present invention the PAC comprises one or more substances selected from the following: acetic acid, phosphoric acid, monobasic phosphate, oxalic acid, malonic acid, salicylic acid, tartaric acid, fumaric acid, citric acid, lactic acid, ascorbic acid, succinic acid, histidine-HCl, or salts of any of the listed acids or combinations of two or more of the aforementioned types of PAC salts. Examples of other PAC ST salts useful in this embodiment of the invention include: (i) acid addition salts formed with inorganic acids, e.g., hydrochloric, hydrobromic, sulfuric, phosphoric or nitric; or organic acids, e.g., acetic, oxalic, tartaric, succinic, maleic, fumaric, gluconic, citric, malic, ascorbic, benzoic, tannic, pamoic, alginic, polyglutamic, naphthalenesulfonic, naphthalene-disulfonic or polygalacturonic; and (ii) combinations of two or more of the aforementioned types of PAC salts.

The substantially non-aqueous carrier (excipient) can be any substance that is biocompatible and liquid or soft enough at the animal's body temperature to release the somatotropin into the animal's bloodstream at a desired rate. The carrier is usually hydrophobic and commonly organic, e.g., an oil or fat of vegetable, animal, mineral or synthetic origin or derivation. Preferably, but not necessarily, the carrier includes at least one chemical moiety of the kind that typifies "fatty" compounds, e.g., fatty acids, alcohols, esters, etc., i.e., a hydrocarbon chain, an ester linkage, or both. "Fatty" acids in this context include acetic, propionic and butyric acids through straight- or branched-chain organic acids containing up to 30 or more carbon atoms. Preferably, the carrier is immiscible in water and/or soluble in the substances commonly known as fat solvents. The carrier can correspond to a reaction product of such a "fatty" compound or compounds with a hydroxy compound, e.g., a monohydric, di-hydric, trihydric or other polyhydric alcohol, e.g., glycerol, propanediol, lauryl alcohol, polyethylene or -propylene glycol, etc. These compounds include the fat-soluble vitamins, e.g., tocopherols and their esters, e.g., acetates sometimes produced to stabilize tocopherols. Sometimes, for economic reasons, the carrier may preferably comprise a natural, unmodified vegetable oil such as sesame oil, soybean oil, peanut oil, palm oil, or an unmodified fat. Alternatively the vegetable oil or fat may be modified by hydrogenation or other chemical means which is compatible with the present invention. The appropriate use of hydrophobic substances prepared by synthetic means is also envisioned.

Compositions of this invention may optionally comprise, in addition to the biocompatible oil, an "antihydration agent" which term as used herein means a substance that retards hydration of a somatotropin and/or the biocompatible oil or fat and thereby further decreases and/or stabilizes the rate of release of the ST from that composition following administration to an animal. A great variety of non-toxic antihydration agents are known. By way of example there are "gelling" agents which, when dispersed, and in some cases heated to dissolve them in the oil, give the body of oil greater visco-elasticity (and therefore greater structural stability) and thereby slow down penetration of the oil by body fluids.

The exact mechanism of these agents in the present invention is not fully understood. Thus it has been observed that certain known "gelling" agents provide the desired antihydration effect even when the oil containing such an agent has not been heated to enhance their gelling effect, or when the gel formation, once formed, has been substantially eliminated (e.g. by shear forces). Also, various antihydration agents that do not have substantial ability to gel the oil are suitable for use in this invention (magnesium stearate is one example).

Exemplary antihydration agents include various polyvalent metal salts or complexes of organic acids, for instance fatty acids having from about 8 (preferably at least about 10) to about 22 (preferably up to about 20) carbon atoms, e.g. aluminum, zinc, magnesium or calcium salts of lauric acid, palmitic acid, stearic acid and the like. Such salts may be mono-, di- or tri-substituted, depending on the valence of the metal and the degree of oxidation of the metal by the acid. Particularly useful are the aluminum salts of such fatty acids. Aluminum monostearate and distearate are particularly preferred antihydration agents. Others that are useful include aluminum tristearate, calcium mono- and distearate, magnesium mono- and distearate and the corresponding palmitates, laurates and the like. In many embodiments, the concentration of such an antihydration agent, based on the weight of the oil plus that agent will be, advantageously, up to about 10% (most typically between about 2% and about 5%), although other concentrations may be suitable in some cases.

In preferred formulations of the instant invention the substantially non-aqueous hydrophobic carrier typically comprises at least about 30%, preferably, at least about 40%; but usually less than about 90% and preferably less than about 80%, by weight, of the composition.

In one preferred embodiment the carrier is selected such that the composition is a creamy suspension at 25° C.; e.g. approximately 95% sesame oil gelled with 5% aluminum monostearate (AlMS).

Dry, solid, pH-adjusted somatotropin can be prepared by lyophilization of appropriate solutions containing the somatotropin and PAC. Alternatively, dry, solid, pH-adjusted ST can be prepared by any other means which provides them in the proper form for use in the present invention.

The compositions of matter described for the instant invention may be prepared by any means or procedure that provides for a composition which delivers the desired enhanced bioavailability of ST at the required levels. In a preferred embodiment of the invention the PAC is added to a ST solution or slurry. Preferably the PAC is added to the ST solution/slurry in an amount effective to adjust and maintain the pH of the solution/slurry so that it is at or near to the isoelectric point (pI) of the ST, at such time as the composition becomes aqueous. Next the pH-adjusted solution/slurry is lyophilized to produce a powder. Finally the pH-adjusted ST powder is mixed with the non-aqueous excipient and the mixture is milled for an appropriate period of time in order to achieve the desired particle size and viscosity of the composition (i.e., a particle size should be small enough to provide a viscosity which allows the formulation to be useful according to the current invention). A discussion of how to achieve the desired particle size may be found in U.S. Pat. No. 5,013,713 to James Mitchell, which is herein incorporated by reference for this purpose. The PAC may be an acid or an acid salt. Preferably the PAC is an acid salt. Even more preferably the PAC is an acid salt which results in a buffered slurry monobasic sodium phosphate, for example.

In an alternative embodiment, dry, solid ST is mixed with a predetermined amount of dry, solid PAC; wherein the PAC is added in an amount effective to adjust and maintain the pH of the composition of matter at about the pI of the ST, at such time as the composition becomes aqueous. Once the desired amount of dry, solid ST and PAC have been combined, the dry, solid ST/PAC mixture is mixed with a substantially non-aqueous carrier and milled as described above.

In another embodiment of the present invention a predetermined amount of dry, solid PAC is mixed with a substantially non-aqueous carrier to form a first suspension. Next, ST is added to the first suspension to form a second suspension and the second suspension is milled as described above. As with previous embodiments the PAC is added in an amount effective to maintain the pH of the composition of matter at or near to the pI of the ST, at such time as the composition becomes aqueous.

In general, the preferred pH range of the ST/PAC compositions of matter of the present invention, at such time as the compositions become aqueous, is the value of the ST's pI plus or minus about 1.0 pH unit. More preferably, the pH range of the ST/PAC compositions of matter of the present invention, at such time as the compositions are becomes aqueous, is the value of the ST's pI plus or minus about 0.5 pH units.

Preferably, in the formulations of the instant invention dry, solid, biologically active ST comprises at least about 10%, preferably at least about 20%, and more typically, at least about 40%, and usually less than about 60%, preferably, less than about 55%, and, even more typically less than about 50%, by weight, of the formulation.

The compositions of the present invention preferably comprise at least about 0.1%, preferably, at least about 0.2%, and usually less than about 10%, preferably about 5% or less, by weight, of dry, solid PAC.

The parenteral administration of the formulations, described herein, to an animal (e.g., a mammal such as a bovine) have shown that the compositions exhibit surprisingly improved bioavailability performance characteristics for delivery of ST when compared to previously available ST formulations.

In particular, they provide a relatively more rapid, yet controlled, release during the first several days after administration without the early release becoming an exaggerated "burst" to the extent that durability of the release is unduly impaired. Typically, in terms its practical effects, the most meaningful measure of the ST release over a given period of time is calculated as the area under the curve ("AUC") illustrating the amount of ST made available by the release (e.g., the serum level of ST in the animal) and/or a physiological consequence of the release (e.g., milk produced or weight gained by an animal in which the ST has been released). Use of the present invention has been found to provide a surprisingly greater AUC for measured serum concentrations, this finding is particularly true for periods of time of 14 days.

Even more surprising is that when the AUC represents the desirable physiological effects of ST release (e.g., the amount of milk produced daily by bovine or other lactating animals) for animals treated with the ST formulations of the present invention, the AUC is not only greater than those of known ST/oil formulations, but also surprisingly greater than would be expected, given the magnitude of the serum ST levels present in the lactating animal. Put another way, this means that the formulations of the present invention not only provide for an enhanced release of ST, but also increase the efficacy of the ST which is released by the formulation. Consequently, despite declining serum ST levels, increased milk production is sustained at a level which is surprisingly high.

Examples of the enhanced physiological effects produced by compositions of the present invention are described in examples 5–7 below. These examples describe the unexpected results of sustained elevated milk production response in lactating animals treated with the ST compositions of the instant invention. In these examples serum ST levels and milk production of animals treated with the compositions of the present invention are compared with the serum ST levels and milk production of animals, that were either un-treated, or were treated with the same dose of the same somatotropin, in a zinc-complex, in a composition which comprised essentially the same carrier, but which has not been pH-adjusted to the isoelectric pH using the same PAC. These examples demonstrate that the animals treated with the ST compositions of the present invention have an unexpectedly high and sustained level of milk production.

Thus the compositions of the instant invention provide both higher serum ST levels and a more sustained elevated milk production response, per milligram of ST administered, than provided by previously know compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Examples of Representative Compositions

Table 1 provides a tabulated summary of exemplary compositions for enhanced bioavailability of ST formulations. The weight percent of the ST, the type of PAC used, and the pH of the ST/PAC solution/slurry are indicated, as is the identity non-aqueous excipient used.

TABLE 1

| PH-Adjusting Constituent | % ST | pH | Hydrophobic Carrier |
|---|---|---|---|
| phosphoric acid | MbST[1] (38%) | ~pH8 | SO:AlMS 95:5[2] |
| phosphoric acid | AbST (46%) | ~pH8 | SO:AlMS 95:5[2] |
| sodium phosphate, monobasic | MbST[1] (38%) | ~pH8 | SO:AlMS 95:5[2] |
| histidine-HCl | MbST[1] (38%) | ~pH8 | SO:AlMS 95:5[2] |

[1]mbST = N-methionyl bovine somatotropin
[2]SO:AlMS 95:5 = sesame oil (95%):aluminum monostearate (5%)

Example 2

Adjustment of ST Solution pH Using an Acid

ST solutions are routinely produced at pH >10 at a concentration ~100 mg/ml. To obtain the desired release profile, the pH may be lowered prior to lyophilization and formulation. Using an acid such as phosphoric acid, the pH of the ST solution may be adjusted to that near the isoelectric point of the ST (typically ~8). Once the desired pH is reached the ST may be lyophilized yielding a dry, solid, powder. This powder may be added to a non-aqueous carrier and milled to a viscous suspension with the desirable range of particle size and viscosity.

One method of achieving the type of pH adjustment needed for various embodiments of the instant invention is outlined below:

Step 1: Start with ST solution at a concentration of 100 mg/ml at a pH of about 10.
Step 2: Add acid to reduce the pH of the ST solution/slurry to a pH of about 8 to 9.
Step 3: Lyophilize the ST solution/slurry.
Step 4: Add non-aqueous carrier to the bead mill.
Step 5: Add the lyophilized ST powder to the non-aqueous carrier in the bead mill.
Step 6: Mill to a desired range of particle size and viscosity.

The procedure described in Steps 1–6 typically results in the production of an injectable or otherwise parenterally administratable ST composition (ST as a solid suspension in a non-aqueous carrier).

Example 3

Adjustment of ST Solution pH Using an Acidic Salt

ST solutions are normally produced at pH >10. To obtain the desired release profile, the pH may be lowered prior to lyophilization and formulation. By adding a predetermined volume of an acidic salt such as monosodium phosphate or histidine hydrochloride to the ST solution, the pH may be adjusted to that near the isoelectric point of the ST (about pH 8). After mixing, ST may be lyophilized yielding a powder. This powder may be added to a non-aqueous carrier and milled to a viscous suspension with the desirable range of particle size and viscosity.

The benefit of this method is that the process is simpler than a monitored pH adjustment. Acidic salt solutions often produce a buffered solution/slurry that allows predetermined amounts to be added while consistently reaching the desired pH range.

One protocol for using an acidic salt to achieve the type of pH adjustment needed for various embodiments of the instant invention is outlined below:

Step 1: Start with ST solution at a concentration of 100 mg/ml at a pH of about 10.
Step 2: Add the acidic salt to reduce the pH of the ST solution/slurry to a pH of about 8 to 9 (may be done in a lyophilizer feed tank).
Step 3: Lyophilize the ST/salt solution/slurry.
Step 4: Add non-aqueous carrier to the bead mill.
Step 5: Add the lyophilized ST/salt powder to the non-aqueous carrier in the bead mill.
Step 6: Mill to a desired range of particle size and viscosity.

Example 4

Addition of Acidic Salt

ST powder is routinely produced at a lyophilizer feed pH>10. Formulations of ST powders produced at pH values closer to the isoelectric point, as described herein, have superior performance to the higher pH powders. Addition of an acidic salt to ST powder lyophilized at a pH>10 during formulation may lower the pH of the ST environment and thus produce this desired benefit. An effective amount of acidic salt, as a dry solid, is mixed with a non-aqueous carrier. The lyophilized ST powder is then added and milled to a viscous suspension with the desirable range of particle size and viscosity. In these formulations, both ST and acidic salt are suspended in the non-aqueous carrier as dry solids.

One protocol for using an acidic salt as described above to achieve the type of pH adjustment needed for various embodiments of the instant invention is outlined below:

Step 1: Add an appropriate non-aqueous carrier to the bead mill.
Step 2: Add an predetermined amount of the salt (i.e. an amount sufficient to reduce the pH of the ST to a pH near the pI of the ST) to the non-aqueous carrier and mill to mix.
Step 3: Add lyophilized ST powder (lyophilized from a ST solution of with a pH of about 10).
Step 4: Mill to a desired range of particle size and viscosity.

Example 5

Performance of Formulations Comprising N-methionyl-bST Powders at Various pH's One of the approaches in establishing a cascade relationship among the animal models for formulation testing is through the use of formulations with wide range release and duration characteristics. Consequently, protein with different physical/chemical properties can be used to modify the protein formulation performance. Lyophilized ST powder preparations made by adjusting the ST solution/slurry to various pH's above or below the ST's isoelectric (pI) point prior to lyophilization are expected to be different in their solubility and stability characteristics. When the pH is at or near the protein's pI, the protein's solubility is generally near its lowest point and less ST will be released into the circulation if parenterally administered to animals. Thus, a ST formulation is expected to be the least effective in animals when the ST preparation has been adjusted to a pH at or near its pI.

With regard to protein stability, when the pH is at or near the protein's pI, the protein's net charge is at its lowest point resulting in lower solubility and more intermolecular hydrophobic aggregation. When the pH is significantly removed from the pI, the protein's net charge will increase accordingly resulting in higher solubility and less intermolecular hydrophobic aggregation. However, protein disulfide exchange and covalent modification are generally faster at alkaline pHs while isomerization and chain cleavage are the predominant degradation reactions at acidic pHs.

The performance of the formulations made from N-methionyl-bST powders lyophilized at various pH units above or below the bST pI (8.3) in animals has been surprising. The performance of a particular formulation in an animal is determined by measuring the animal's blood bST concentrations over time and then calculating the area under the curve (AUC) for such a concentration vs. time plot.

Significantly, pH adjusted bST formulations exhibit a surprisingly elevated bST release in rodents and calves in comparison to POSILAC® bovine somatotropin, a commercially available suspension of N-methionine bST is sesame oil containing aluminum monostearate. In particular the formulations with a pH at or near pH 8 exhibit the best performance.

Table 2 shows the bST lyophilization pHs, and the corresponding relative AUC values for bST serum levels in rodents or in calves treated with various formulations. The highest AUCs were obtained with a formulation pH of approximately pH 8. As noted above, this result is opposite to what would be expected based on the known relationship between the protein solubility and pH.

TABLE 2

| pH | Relative bST Serum Concentrations (AUC compared to 1.00 for POSILAC ®) | |
|---|---|---|
|  | Rodents | Calves |
| 10.5 | 1.20 | 1.65 |
| 9.31 | 1.33 | — |
| 8.1 | 1.62 | 1.76 |
| 7.1 | 1.31 | 1.47 |
| 6.0 | 1.34 | — |
| 4.5 | 1.09 | 1.18 |

Example 6

Performance of pH Adjusted Formulations Comprising N-methionyl-bST Versus POSILAC®

The performance improvement, compared with POSILAC®, of the formulations made from N-methionyl-bST powders lyophilized at pH 8 is illustrated by the performance of two lots (NBP 6207845-E & 6446926). In preparation, the bST solutions had an initial pH of 10.5, phosphoric acid was added to bring the pH to about 8, the protein slurry was lyophilized and then the lyophilized bST powder was formulated by following the POSILAC® formulation procedure. The formulation lots contain approximately 38% dry solid bovine bST and 0.3% phosphates in the typical POSILAC® excipient (i.e., 95% sesame oil gelled with 5% aluminum monostearate).

Both the pH-adjusted bST formulations and POSILAC® were parenterally administered to rodents and calves. The mean serum bST concentrations were measured over 14 days following administration of the formulations are shown in FIGS. 1 and 2, for rodents and calves respectively. In rodents, the bST was released more rapidly from the pH-adjusted bST formulations than from the POSILAC®. In calves, the formulation exhibited a larger burst, yet also maintained extended release comparable to POSILAC®.

As shown in FIG. 3, concentration of serum bST levels in pH-adjusted formulation treated dairy cows were increased when compared with dairy cows treated with an identical amount of bST using the POSILAC® formulation. Over two 14-day cycles, the bST AUC ratio for pH-adjusted formulation to POSILAC® is calculated to be 1.6. This indicates that adjustment of the pH to near the bST's pI during the formulation of the composition improves the bST release into the circulatory system and results in a 60% increase in bST bioavailability in target animals when compared with POSILAC®.

Following administration of the pH-adjusted bST formulation, milk production increased and continued to be elevated above levels attained in dairy cows treated with an identical amount of bST, administered as the POSILAC® formulation. Milk production was monitored throughout six cycles 14-day treatment cycles. As shown in FIG. 4, dairy cows treated with the pH-adjusted bST formulation exhibited a sustained elevated milk response throughout the six 14-day cycles. It should be noted that dairy cattle treated with the pH-adjusted formulation exhibited surprisingly increased milk production levels. Over the entire trial period, six 14-day cycles, the overall milk yield was 5 pounds per day higher than that in dairy cows treated with an identical amount of bST in the POSILAC® formulation.

Particularly surprising is the observation that increased milk production is maintained in animals treated with the pH-adjusted bST formulation, despite the fact that serum bST levels, in cows treated with POSILAC®, the pH-adjusted bST formulation (lot #NBP66446926), or the negative control are nearly identical at the end of each 14-day cycle. These data clearly demonstrate a sustained elevated milk production response for the animals treated with the pH-adjusted bST formulations.

Example 7

Performance of pH Adjusted Formulations Comprising N-alanyl-bST Versus POSILAC®

The performance improvement of the formulations made from N-alanyl-bST powders lyophilized at various pH's when compared with an identical amount of bST delivered as a POSILAC® formulation is illustrated by a rat growth assay. The rat growth assay was used to measure the biological potency of the ST/PAC formulations of the present invention. As used here the term "biological potency" denotes the capacity of the ST/PAC formulations to accelerate weight gain in rodents treated therewith.

Rodents were injected subcutaneously with 25 mg of the bST/PAC formulations and the rodent's daily weights were followed for 15 days. Table 3 lists the formulation administered, the relative potency, versus POSILAC®, and the 95% confidence interval for relative potency. The formulation with a pH near 8 was most effective at stimulating rodent growth as measured by this assay.

TABLE 3

Relative Potency and 95% Confidence Interval of Various Test Lots

| Lot No. | Description | Relative Potency | Lower Limit | Upper Limit |
|---|---|---|---|---|
| 95E02/10 | POSILAC ® | 100.0 | 92.6 | 107.4 |
| 6393359 | 46% abST[1] (pH 10.7) in SO/AlMS[2] | 100.7 | 90.9 | 110.6 |
| 6393361 | 46% abST[1] (pH 8.9) in SO/AlMS[2] | 129.9 | 117.8 | 142.0 |
| 6393363 | 46% abST[1] (pH 8.0) in SO/AlMS[2] | 139.8 | 131.1 | 148.4 |
| 6393367 | 46.5% abST[1] (pH 10.7) + 5% $NaH_2PO_4$ in sesame oil | 126.0 | 116.5 | 135.5 |
| 6393369 | 49.2% abST[1] (pH 8.9) in sesame oil | 137.7 | 129.4 | 146.1 |

[1]abST = N-alanyl-bovine somatotropin
[2]SO/AlMS = sesame oil/aluminum monostearate

Example 8

Pharmicokinetic Studies in Rodents for a Variety of Compositions

Rodents were injected subcutaneously with 15 mg of pH-adjusted bST (mixed with the various PAC's described) according to the following protocol.

Test Subjects:
Mature female Sprague-Dawley rats, 12–13 weeks of age, ~250 g.

Control Group:
Six (6) rats treated with reference standard material.

Treated Groups:
Six (6) rats per test article (formulation lot), randomly assigned. Animals were assigned to treatment groups using a completely randomized design according to body weight on Day −1 or Day 0 prior to treatment initiation. A weight range of 250+/−20 gram was used.

Test Articles:
POSILAC®, as a positive control, and various pH-adjusted bST formulations were studied.

Section B: Weighing, Dosing, Blood Collection, and Sample Shipment Weighing:
Animals were weighed on Day −1 or Day 0 for randomization and treatment assignment. A final weight was taken on Day 14 following the final blood sample collection.

Route of Injection:
Subcutaneous (SC) injection in the dorsal suprascapular region. Injections were administered with 1 cc tuberculin syringes with 18 G 1.5-inch needles for all formulations.

Dose Volumes:
15 mg of bST with the dose volume of ~0.04 ml were administered to each rat on Day 0. A fill volume of ~0.08 ml was prepared to adjust for the amount of formulation remaining in the needle following the injection. The time of injection was recorded for each individual rat. Syringes were weighed both prior to and following injection to determine the weight of the protein injected.

Blood Collection:
Blood samples were collected via retro-orbital bleeds, using alternating eyes at the various time-points, following anesthesia with $CO_2/O_2$ (80/20) gas. EDTA coated or non-coated micro-hematocrit capillary tubes were used for the blood collections. The whole blood was transferred to blood plasma separator tubes (Microtainer® with EDTA, lavender; MFG# BD5960). The blood was then centrifuged at 6000 g for 10 minutes at room temperature. Samples were stored frozen at −20° C.

Blood Volumes:
It was necessary to obtain a minimum of 200 μl of whole blood at each time point from each rat in order to have 100 μl of plasma. A total volume of 300 μl of whole blood is preferable to ensure an adequate plasma volume.

Blood Collection Time Points:
Blood samples were collected at 11 time points, 7 different time points for each rat, following the sampling scheme outlined in the Rat Blood Sampling Schedule (below). The time of collection were recorded for each individual rat.

Blood Collection Time Points:
Day 0, prior to injection 4, 8, and 12 hours post-injection (after the injection)
Day 1 (24 hr)
Day 2 (48 hr)
Day 5 (120 hr)
Day 7 (168 hr)
Day 9 (216 hr)
Day 12 (288 hr)
Day 14 (336 hr)

Note: All blood collections were within+/−one (1) hour.

Rat Blood Sampling Schedule:

|  | Rat # | | | | | |
| --- | --- | --- | --- | --- | --- | --- |
| Time | 1 | 2 | 3 | 4 | 5 | 6 |
| 0 | X | X | X | X | X | X |
| 4 hr | X |   | X |   | X |   |
| 8 hr | X | X |   | X |   |   |
| 12 hr |   | X | X |   |   | X |
| Day 1 (24 hr) |   |   |   | X | X | X |
| Day 2 (48 hr) | X | X | X |   |   |   |
| Day 5 (120 hr) |   | X |   | X | X | X |
| Day 7 (168 hr) | X |   | X | X | X |   |
| Day 9 (216 hr) |   | X |   | X |   | X |
| Day 12 (288 hr) | X |   | X |   | X | X |
| Day 14 (336 hr) | X | X | X | X | X | X |

Note:
This scheme gives seven (7) bleeds per rat over a 14 day period.

Serum samples were collected and analyzed for bST levels.

All of the compositions and methods disclosed and claimed herein can be made and executed without undue experimentation in light of the present disclosure. While the compositions and methods of this invention have been described in terms of preferred embodiments, it will be apparent to the skilled artisan that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Dong et al., WO 00/13674; March/2000;A61K 9/20, 9/48
Ewuribe, U.S. Pat. No. 5,359,030; October/1994; 530/303
Ewuribe, U.S. Pat. No. 5,438,040; August/1995; 514/3
Ewuribe, U.S. Pat. No. 5,681,811; October/1997; 514/8
Christensen et al., WO 97/03692; February/1997; A61K 38/27, 33/30
Furguson et al., U.S. Pat. No. 4,977,140; December/1990; 514/12
Hamilton et al., U.S. Pat. No. 4,816,568; March/1989; 530/399
Kim et al., U.S. Pat. No. 5,520,927; May/1996; 424/450
Kim et al., U.S. Pat. No. 5,744,163; April/1998; 424/489
Krivi, G. G., U.S. Pat. No. 5,399,489; March/1995; 435/172.3
Krivi, G. G., U.S. Pat. No. 5,744,328; April/1998; 435/69.4
Magruder et al., U.S. Pat. No. 5,034,229; July/1991; 424/422
Martin, EP 0 216 485; April/1987; C 07 G 15/00
Mitchell, U.S. Pat. No. 5,739,108; April/1998; 514/12
Pikal et al., U.S. Pat. No. 5,612,315; March/1997; 514/21
Raman et al., U.S. Pat. No. 5,356,635; October/1994; 424/484
Raman et al., WO 93/13792; July/1993
Seeley et al., WO 93/19773; October/1993
Sivaramakrishnan et al., U.S. Pat. No. 5,219,572; June/1993; 424/438
Sørensen et al., WO 93/12812; July/1993; A61K 37/36
Sørensen et al., U.S. Pat. No. 5,849,704; December/1998; 514/12
Steber et al., EP 0 523 330 A1; January/1993; A61K 9/00
Storrs et al., U.S. Pat. No. 5,986,073; November/1999; 530/419
Tyle, U.S. Pat. No. 4,857,506; August/1989; 514/12
Viswanathan et al., U.S. Pat. No. 4,917,685; April/1990; 604/891.1

What is claimed is:

1. A method which comprises parenterally administering to a mammal a substantially non-aqueous composition of matter comprising:
   somatotropin (ST) and a pH-adjusting constituent (PAC);
   wherein the PAC is present in an amount effective to maintain the pH of the composition of matter at or near to the isoelectric point (pI) of the ST, at such time as the composition of matter becomes aqueous; and
   wherein the somatotropin and the PAC are suspended in a substantially non-aqueous hydrophobic carrier.

2. The method of claim 1 wherein the somatotropin (ST) is present in the composition at from about 10% to about 60%, by weight; the pH-adjusting constituent (PAC) is present in an amount effective to maintain the pH of the composition of matter within about 1.0 pH units of the isoelectric point of the ST; and the substantially non-aqueous hydrophobic carrier is present at from about 30% to about 90%, by weight.

3. The method of claim 1 wherein the somatotropin (ST) is present in the composition at from about 20% to about 55%, by weight; the pH-adjusting constituent (PAC) is present in an amount effective to maintain the pH of the composition of matter within about 0.5 pH units of the isoelectric point of the ST; and the substantially non-aqueous hydrophobic carrier is present at from about 40% to about 80%, by weight.

4. The method of claim 1 wherein the somatotropin (ST) is an N-alanyl-ST or an N-methionyl-ST present in the composition at from about 20% to about 55%, by weight;
   the pH-adjusting constituent (PAC) is comprised of one or more of the following: acetic acid, phosphoric acid, monobasic phosphate, and histidine-HCl;
   wherein the PAC is present in an amount effective to maintain the pH, of the composition of matter within about 0.5 pH units of the isoelectric point of the ST; and
   wherein the substantially non-aqueous hydrophobic carrier is present at from about 40% to about 80%, by weight; wherein the non-aqueous hydrophobic carrier is comprised of about 95% to 100% sesame oil and, optionally, up to about 5% aluminum monostearate.

5. The method of 1 wherein the composition of matter is parenterally administered to the mammal in order to induce improved weight gain or elevated milk production in the mammal.

6. The method of claim 1 wherein the somatotropin (ST) is an N-methionyl-ST or N-alanyl-ST.

7. The method of claim 1 wherein the somatotropin (ST) is human, equine, bovine, or porcine somatotropin.

8. The method of claim 7 wherein the somatotropin (ST) is human or bovine somatotropin.

9. The method of claim 1 wherein the pH-adjusting constituent is selected from one or more of the following compounds: acetic acid, phosphoric acid, monobasic phosphate and histidine-HCl.

10. The method of claim 1 wherein the pH-adjusting constituent is present in an amount effective to maintain the pH of a the composition of matter within about 1.0 pH units of the isoelectric point (pI) of the ST.

11. The method of claim 10 wherein the pH-adjusting constituent is present in an amount effective to maintain the pH of the composition of matter within about 0.5 pH units of the isoelectric point (pI) of the ST.

12. The method of claim 1 wherein the substantially non-aqueous hydrophobic carrier comprises an oil or a fat.

13. The composition of matter of claim 12 wherein the hydrophobic carrier comprises sesame oil and aluminum monostearate.

14. The method of claim 13 wherein the hydrophobic carrier is comprised of about 95%, sesame oil and about 5% aluminum monostearate.

15. The method of claim 1 wherein the substantially non-aqueous hydrophobic carrier is present at from about 30% to about 90% by weight, of the composition.

16. The method of claim 15 wherein the substantially non-aqueous hydrophobic carrier is present from about 40% to about 80% by weight, of the composition.

17. The method of claim 1 wherein the somatotropin is present at from about 10% to about 60% by weight.

18. The method of claim 17 wherein the somatotropin is present at from about 20% to about 55% by weight.

19. The method of claim 1 wherein the pH-adjusting constituent is present from about 0.1 to about 10% by weight, of the composition.

20. The method of claim 19 wherein the pH-adjusting constituent is present from about 0.2 to about 5% by weight.

21. The method of claim 1, wherein the somatotropin is N-alanyl bovine somatotropin or N-methionyl bovine somatotropin present at from about 20% to about 55%, by weight; and wherein the pH-adjusting constituent is present in an amount effective to maintain the pH, of the composition of matter within about 0.5 pH units of the isoelectric point (pI) of the ST.

22. A method for sustaining elevated milk production response in a lactating mammal comprising:

parenterally administering to the mammal a substantially non-aqueous, biocompatible composition of matter comprising:

a somatotropin (ST), active in the mammal, and a pH-adjusting constituent (PAC);

wherein the PAC is present in an amount effective to maintain the pH of the composition of matter at or near to the isoelectric point (pI) of the ST, at such time as the composition of matter becomes aqueous;

wherein the PAC comprises one or more of the following: acetic acid, phosphoric acid, monobasic phosphate, and histidine HCl; and wherein the somatotropin and the PAC are suspended in a substantially non-aqueous hydrophobic carrier.

* * * * *

UNITED STATES PATENT AND TRADEMARK OFFICE
CERTIFICATE OF CORRECTION

| | | |
|---|---|---|
| PATENT NO. | : 7,030,091 B2 | Page 1 of 1 |
| APPLICATION NO. | : 10/691425 | |
| DATED | : April 18, 2006 | |
| INVENTOR(S) | : Daniel N. Heintz and Yunhua N. Jeng | |

It is certified that error appears in the above-identified patent and that said Letters Patent is hereby corrected as shown below:

Drawings Sheet 1, Fig. 1, delete the first line of the legend and replace it with --Figure 1: Comparison of bST Release Profiles in Rodents--.

Drawings Sheet 2, Fig. 3, delete the first line of the legend and replace it with --Figure 3: Comparison of bST Release Profiles in Cows--.

Column 1, Line 7, after "now" delete [S.].

Column 19, Line 1, after "of" first occurrence add --claim--.

Column 19, Line 29, after "95%" delete the comma [,].

Signed and Sealed this

Fifth Day of February, 2008

JON W. DUDAS
*Director of the United States Patent and Trademark Office*